United States Patent
Quintana Romero et al.

(10) Patent No.: US 12,343,316 B2
(45) Date of Patent: Jul. 1, 2025

(54) CANNABIDIOL AND/OR DERIVATIVES THEREOF FOR USE IN THE TREATMENT OF MITOCHONDRIAL DISEASES

(71) Applicant: UNIVERSITAT AUTONOMA DE BARCELONA, Barcelona (ES)

(72) Inventors: Albert Quintana Romero, Barcelona (ES); Elisenda Sanz Iglesias, Girona (ES); Emma Puighermanal, Barcelona (ES)

(73) Assignee: UNIVERSITAT AUTÓNOMA DE BARCELONA, Barcelona (ES)

( * ) Notice: Subject to any disclaimer, the term of this patent is extended or adjusted under 35 U.S.C. 154(b) by 933 days.

(21) Appl. No.: 17/310,181

(22) PCT Filed: Jan. 24, 2020

(86) PCT No.: PCT/EP2020/051772
§ 371 (c)(1),
(2) Date: Jul. 23, 2021

(87) PCT Pub. No.: WO2020/152336
PCT Pub. Date: Jul. 30, 2020

(65) Prior Publication Data
US 2022/0096395 A1    Mar. 31, 2022

(30) Foreign Application Priority Data
Jan. 25, 2019   (EP) ..................... 19382053

(51) Int. Cl.
*A61K 31/05*    (2006.01)
*A61K 31/122*   (2006.01)
*A61P 39/00*    (2006.01)

(52) U.S. Cl.
CPC ............ *A61K 31/05* (2013.01); *A61K 31/122* (2013.01); *A61P 39/00* (2018.01)

(58) Field of Classification Search
CPC ........ A61K 31/05; A61K 31/122; A61P 39/00
See application file for complete search history.

(56) References Cited

U.S. PATENT DOCUMENTS

2021/0015789 A1* 1/2021 Guy ................... B01D 11/0288

FOREIGN PATENT DOCUMENTS

| WO | 2012019029 A2 | 2/2012 |
| WO | 2012019032 A1 | 2/2012 |
| WO | 2014011047 A1 | 1/2014 |
| WO | 2019207319 A1 | 10/2019 |

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Muraresku et al. Current Genetic Medicine Reports (2018) 6:62-72). (Year: 2018).*
Johri et al. J Pharmacol Exp Ther. 2012; 342(3): 619-630 (Year: 2012).*
Quintana et al., "Lack of GPR88 enhances medium spiny neuron activity and alters motor- and cue-dependent behaviors", Nature Neuroscience, vol. 15, No. 11, pp. 1547-1557, Nov. 2012.
Rajan et al., "Gingival stromal cells as an in vitro model: Cannabidiol modulates genes linked with Amyotrophic Lateral Sclerosis", Journal of Cellular Biochemistry, pp. 1-27, 2016.
Reardon et al., "Diabetes mellitus associated with a pathogenic point mutation in mitochondrial DNA", Lancet, vol. 340, pp. 1376-1379, 1992.
Rimmerman et al., "Direct modulation of the outer mitochondrial membrane channel, voltage-dependent anion channel 1 {VDAC1) by cannabidiol: a novel mechanism for cannabinoid-induced cell death", Cell Death and Disease, vol. 4, e949, pp. 1-11, 2013.
Rosado, Dr. Joseph, "Medical Marijuana and Mitochondrial Disease", https://www.marijuanadoctors.com/conditions/mitochondrial-disease/, pp. 1-6, 2021.
Ryan et al., "Cannabidiol Targets Mitochondria to Regulate Intracellular Ca2+ Levels", The Journal of Neuroscience, vol. 29, No. 7, pp. 2053-2063, 2009.
Scacco et al., "Pathological Mutations of the Human NDUFS4 Gene of the 18-kDa (AQDQ) Subunit of Complex I Affect the Expression of the Protein and the Assembly and Function of the Complex", The Journal of Biological Chemistry, vol. 278, No. 45, Issue of Nov. 7, pp. 44161-44167, 2003.
Schapira et al., "Mitochondrial Complex I Deficiency in Parkinson's Disease", Journal of Neurochemistry, vol. 54, No. 3, pp. 823-827, 1990.
Shoffner et al., "Myoclonic Epilepsy and Ragged-Red Fiber Disease (MERRF) Is Associated with a Mitochondrial DNA tRNALys Mutation", Cell, vol. 61, pp. 931-937, 1990.
Shoffner et al., "Invited Editorial Mitochondrial Genetics: Principles and Practice", Am. Hum. Genet., vol. 51, pp. 1179-1186, 1992.
Singh et al., "Cannabinoid-Induced Changes in the Activity of Electron Transport Chain Complexes of Brain Mitochondria", J. Mol. Neurosci., pp. 1-6, 2015.

(Continued)

*Primary Examiner* — Brandon J Fetterolf
*Assistant Examiner* — Jerica Katlynn Wilson
(74) *Attorney, Agent, or Firm* — McKee, Voorhees & Sease, PLC

(57) ABSTRACT

The invention relates to the use of cannabidiol (CBD) and/or a derivative thereof, in the treatment of mitochondrial diseases. In certain preferred embodiments, the CBD, and/or a derivative thereof is substantially devoid of tetrahydrocannabinol (THC). Moreover, the present invention also relates to a composition comprising the CBD and/or a derivative thereof and to a method of treating mitochondrial diseases in a subject, comprising administering to the subject in need thereof a therapeutically effective amount of the CBD, a derivative thereof and/or a composition comprising thereof.

9 Claims, 3 Drawing Sheets

(56) References Cited

OTHER PUBLICATIONS

Sun et al., "Cannabidiol attenuates OGD/R-induced damage by enhancing mitochondrial bioenergetics and modulating glucose metabolism via pentose-phosphate pathway in hippocampal neurons", Redox Biology, vol. 11, pp. 577-585, 2017.
Taivassalo et al., "Endurance training and detraining in mitochondrial myopathies due to single large-scale mtDNA deletions", Brain, vol. 129, pp. 3391-3401, 2006.
Valvassori et al., "Acute and chronic administration of cannabidiol increases mitochondrial complex and creatine kinase activity in the rat brain", Revista Brasileira de Psiquiatria, vol. 35, pp. 380-386, 2013.
Viscomi et al., "In Vivo Correction of COX Deficiency by Activation of the AMPK/PGC-1α Axis", Cell Metabolism, vol. 14, No. 1, pp. 80-90, 2011.
Wasniewska et al., "Abnormal Calcium Homeostasis in Fibroblasts from Patients with Leigh Disease", Biochemical and Biophysical Research Communications, vol. 283, pp. 687-693, 2001.
Wedding et al., "Spastic Paraplegia Type 7 Is Associated with Multiple Mitochondrial DNA Deletions", PLoS One, vol. 9, Issue 1, e86340, pp. 1-8, Jan. 2014.
Wikipedia—"NDUFS4", pp. 1-12, 2021.
Wikipedia—"Kearns-Sayre syndrome", pp. 1-8, 2021.
Wikipedia—"Neuropathy, ataxia, and retinitis pigmentosa", pp. 1-4, 2021.
Wu et al., "Cannabidiol induced apoptosis in human monocytes through mitochondrial permeability transition pore-mediated ROS production", Free Radic Biol Med., pp. 1-39, 2018.
Yatsuga et al., "Effect of bezafibrate treatment on late-onset mitochondrial myopathy in mice", Human Molecular Genetics, vol. 21, No. 3, pp. 526-535, 2012.
Yu-Wai-Man et al., "Inherited mitochondrial optic neuropathies", J Med Genet, vol. 46, pp. 145-158, 2009.
Online Mendelian Inheritance in Man, OMIM, John Hopkins University, Baltimore, MD., MIM No. 203700; date last edited: Feb. 24, 2015; downloaded from the World Wide Web URL: https://omim.org/ on Dec. 29, 2021.
Online Mendelian Inheritance in Man, OMIM, Johns Hopkins University, Baltimore, MD., MIM No. 256000, date last edited: Dec. 6, 2018, downloaded from the World Wide Web URL: https://omim.org/ on Dec. 29, 2021.
Online Mendelian Inheritance in Man, OMIM, Johns Hopkins University, Baltimore, MD., MIM No. 520000, date last edited: Oct. 31, 2012, downloaded from the World Wide Web URL: https://omim.org/ on Dec. 29, 2021.
Online Mendelian Inheritance in Man, OMIM, Johns Hopkins University, Baltimore, MD., MIM No. 530000, date last edited: Apr. 21, 2006, downloaded from the World Wide Web URL: https://omim.org/ on Dec. 29, 2021.
Online Mendelian Inheritance in Man, OMIM, Johns Hopkins University, Baltimore, MD., MIM No. 535000, date last edited: Aug. 26, 2011, downloaded from the World Wide Web URL: https://omim.org/ on Dec. 29, 2021.
Online Mendelian Inheritance in Man, OMIM, Johns Hopkins University, Baltimore, MD., MIM No. 540000, date last edited: Jan. 20, 2016; downloaded from the World Wide Web URL: https://omim.org/ on Dec. 29, 2021.
Online Mendelian Inheritance in Man, OMIM, Johns Hopkins University, Baltimore, MD., MIM No. 545000, date last edited: Nov. 19, 2014, downloaded from the World Wide Web URL: https://omim.org/ on Dec. 29, 2021.
Online Mendelian Inheritance in Man, OMIM, Johns Hopkins University, Baltimore, MD., MIM No. 551500, date last edited: Nov. 10, 2009, downloaded from the World Wide Web URL: https://omim.org/ on Dec. 29, 2021.
Online Mendelian Inheritance in Man, OMIM, Johns Hopkins University, Baltimore, MD., MIM No. 557000, date last edited: Jul. 31, 2007, downloaded from the World Wide Web URL: https://omim.org/ on Dec. 29, 2021.
Online Mendelian Inheritance in Man, OMIM, Johns Hopkins University, Baltimore, MD., MIM No. 614739, date last edited: Feb. 19, 2018, downloaded from the World Wide Web URL: https://omim.org/ on Dec. 29, 2021.
Aso et al., "Cannabinoids for treatment of Alzheimer's disease: moving toward the clinic", Frontiers in Pharmacology, vol. 5, Article 37, pp. 1-11, Mar. 2014.
Baertling et al., "NDUFAF4 variants are associated with Leigh syndrome and cause a specific mitochondrial complex I assembly defect", European Journal of Human Genetics, vol. 25, pp. 1273-1277, 2017.
Ballinger et al., "Maternally transmitted diabetes and deafness associated with a 10.4 kb mitochondrial DNA deletion", Nature Genetics, vol. 1, pp. 11-15, Apr. 1992.
Bilkei-Gorzo, Andras, "The endocannabinoid system in normal and pathological brain ageing", Phil. Trans. R. Soc. B, vol. 367, pp. 3326-3341, 2012.
Blanchet et al., "Quantifying small molecule phenotypic effects using mitochondrial morpho-functional fingerprinting and machine learning", Scientific Reports, vol. 5, No. 8035, pp. 1-7, 2015.
Bolea et al., "Defined neuronal populations drive fatal phenotype in a mouse model of Leigh syndrome", eLIFE, vol. 8, e47163, pp. 1-26, 2019.
Cejudo et al., "Exercise Training in Mitochondrial Myopathy: A Randomized Controlled Trial", Muscle Nerve, vol. 32, pp. 342-350, 2005.
Cohen et al., "POLG-Related Disorders", GeneReviews, pp. 1-32, 2010.
Desprez, Tifany, "Role(s) of the mitochondrial type-1 cannabinoid receptor in the brain", HAL Open Science, pp. 1-256, 2015.
Devitt-Lee, Adrian, "CBD Science: How Cannabinoids Work at the Cellular Level to Keep You Healthy", https://www.alternet.org/2016/12/cbd-science-mitochondria-mysteries-homeostasis-renewal-endocannabinoid-system/, pp. 1-11, 2016.
Distelmaier, et al., "Trolox-Sensitive Reactive Oxygen Species Regulate Mitochondrial Morphology, Oxidative Phosphorylation and Cytosolic Calcium Handling in Healthy Cells", Antioxidants & Redox Signaling, vol. 17, No. 12, pp. 1657-1669, 2012.
Fadic et al., "Sensory ataxic neuropathy as the presenting feature of a novel mitochondrial disease", Neurology, vol. 49, pp. 239-245, 1997.
Feng et al., "Effects of dimethylglycine sodium salt supplementation on growth performance, hepatic antioxidant capacity, and mitochondria-related gene expression in weanling piglets born with low birth weight1", J. Anim. Sci., vol. 96, pp. 3791-3803, 2018.
Fišar et al., "Cannabinoid-induced changes in respiration of brain mitochondria", Toxicology Letters, vol. 231, pp. 62-71, 2014.
Giorgi et al., "Mitochondrial calcium homeostasis as potential target for mitochondrial medicine", Mitochondrion, vol. 12, pp. 77-85, 2012.
Goldstein et al., "Mitochondrial DNA Deletion Syndromes", Gene Reviews, pp. 1-21, 2003.
Guillausseau et al., "Maternally Inherited Diabetes and Deafness: A Multicenter Study", Annals of Internal Medicine, vol. 134, pp. 721-728, 2001.
Haginoya et al., "Efficacy of idebenone for respiratory failure in a patient with Leigh syndrome: A long-term follow-up study", Journal of the Neurological Sciences, vol. 278, pp. 112-114, 2009.
Ibeas-Bih et al., "Molecular Targets of Cannabidiol in Neurological Disorders", Neurotherapeutics, vol. 12, pp. 699-730, 2015.
Jauslin et al., "Mitochondria-targeted antioxidants protect Friedreich Ataxia fibroblasts from endogenous oxidative stress more effectively than untargeted antioxidants", FASEB Journal, vol. 17, No. 13, pp. 1-10, 10.1096/j.03-0240fje. published online Aug. 15, 2003.
Jeppesen et al., "Aerobic training is safe and improves exercise capacity in patients with mitochondrial myopathy", Brain, vol. 129, pp. 3402-3412, 2006.
Johnson et al., "mTOR Inhibition Alleviates Mitochondrial Disease in a Mouse Model of Leigh Syndrome", Science, vol. 342, No. 6165, pp. 1524-1528, Dec. 20, 2013.
Jurisch-Yaksi et al., "Spatially organized ciliary beating in ependymal cells compaitmentalizes CSF flow in the brain and regulate ventricular development", Current Biology, pp. 1-2, 2018.

(56) References Cited

OTHER PUBLICATIONS

Khan et al., "Effective treatment of mitochondrial myopathy by nicotinamide riboside, a vitamin B3", EMBO Molecular Medicine, vol. 6, No. 6, pp. 721-731, 2014.

Komen et al., "Turn up the power-pharmacological activation of mitochondrial biogenesis in mouse models", British Journal of Pharmacology, vol. 171, pp. 1818-1836, 2014.

Kruse et al., "Mice with Mitochondrial Complex I Deficiency Develop a Fatal Encephalomyopathy", Cell Metab., vol. 7, No. 4, pp. 312-320, Apr. 2008.

Lake et al., "Leigh Syndrome: One Disorder, More Than 75 Monogenic Causes", Ann Neurol., vol. 79, pp. 190-203, 2016.

Leitão-Rocha et al., "Trends in Mitochondrial Therapeutics for Neurological Disease", Current Medicinal Chemistry, vol. 22, pp. 2458-2467, 2015.

Liet et al., "The Effect of Short-Term Dimethylglycine Treatment on Oxygen Consumption in Cytochrome Oxidase Deficiency: a Double-Blind Randomized Crossover Clinical Trial", J. Pediatr, vol. 142, pp. 62-66, 2003.

Lipina et al., "Mitochondria: a possible nexus for the regulation of energy homeostasis by the endocannabinoid system?", Am J. Physiol Endocrinol Metab., vol. 307, pp. E1-E13, 2014.

Liu et al., "Glial Lipid Droplets and ROS Induced by Mitochondrial Defects Promote Neurodegeneration", Cell, vol. 15, No. 160(0), pp. 177-190, 2015.

Loeffen et al., "Isolated Complex I Deficiency in Children: Clinical, Biochemical and Genetic Aspects", Human Mutation, vol. 15, pp. 123-134, 2000.

Maas et al., "Progressive Deafness—Dystonia Due to SERAC1 Mutations: A Study of 67 Cases", Ann Neurol., vol. 82, pp. 1004-1015, 2017.

Majdi et al., "Cannabinoids Δ9-tetrahydrocannabinol and cannabidiol may be effective against methamphetamine induced mitochondrial dysfunction and inflammation by modulation of Toll-like type-4(Toll-like 4) receptors and NF-κB signaling", Medical Hypotheses, vol. 133, p. 109371, 2019.

Martin et al., "Leigh Syndrome Associated With Mitochondrial Complex I Deficiency Due to a Novel Mutation in the NDUFS1 Gene", Arch Neurol., vol. 62, pp. 659-661, 2005.

Maternally-Inherited Leigh Syndrome (Concept Id: C2931092)—MedGen—NCBI, pp. 1-3, 2021.

Milone et al., "Polymerase Gamma 1 Mutations: Clinical Correlations", The Neurologist, vol. 16, No. 2, pp. 84-91, 2010.

Mitochondrial Disease—Medical Marijuana Inc., (OTC MJNA), pp. 1-2, 2015.

Montagna et al., "Mitochondrial Abnormalities in Migraine. Preliminary Findings.", Headache The Journal of Head and Face Pain, pp. 1-4, 1988.

Murayama et al., "Recent topics: the diagnosis, molecular genesis, and treatment of mitochondrial diseases", Journal of Human Genetics, vol. 64, pp. 113-125, 2019.

Nunn et al., "Endocannabinoids in neuroendopsychology: multiphasic control of mitochondrial function", Phil. Trans. R. Soc. B, vol. 367, pp. 3342-3352, 2012.

Olivas-Aguirre et al., "Cannabidiol directly targets mitochondria and disturbs calcium homeostasis in acute lymphoblastic leukemia", Cell Death and Disease, vol. 10, No. 779, pp. 1-19, 2019.

Orphanet: Congenital lactic acidosis, Saguenay Lac Saint Jean type, pp. 1-3, 2021.

Papadimitriou et al., "Partial depletion and multiple deletions of muscle mtDNA in familial MNGIE syndrome", Neurology, vol. 51, pp. 1086-1092, 1998.

Parikh et al., "A Modern Approach to the Treatment of Mitochondrial Disease", Curr Treat Options Neural., vol. 11, No. 6, pp. 414-430, Nov. 2009.

Pavlakis et al., "Mitochondrial Myopathy, Encephalopathy, Lactic Acidosis, and Strokelike Episodes: A Distinctive Clinical Syndrome", Annals of Neurology, vol. 16, No. 4, pp. 481-488, Oct. 1984.

Peres et al., "Cannabidiol as a Promising Strategy to Treat and Prevent Movement Disorders?", Frontiers in Pharmacology, vol. 9, Article 482, pp. 1-12, May 2018.

Pfeffer et al., "Treatment for mitochondrial disorders", Cochrane Library, pp. 1-39, 2012.

Puighermanal et al., "Ribosomal Protein S6 Phosphorylation Is Involved in Novelty-Induced Locomotion, Synaptic Plasticity and mRNA Translation", Frontiers in Molecular Neuroscience, vol. 10, Article 419, pp. 1-16, Dec. 2017.

Quintana et al., "Complex I deficiency due to loss of Ndufs4 in the brain results in progressive encephalopathy resembling Leigh syndrome", PNAS, vol. 107, No. 24, pp. 10996-11001, Jun. 2010.

203700—Mitochondrial DNA Depletion Syndrome 4A (Alpers Type); MTDPS4A, Datasheet [online], OMIM, Creation date: Jun. 1986 [retrieved on Aug. 27, 2024]. Retrieved from the Internet:<URL:https://omim.org/entry/203700>, 4 pages.

614739-3—Methylglutaconic Aciduria With Dystonia-Deafness, Hepatopathy, Encephalopathy, and Leigh-Like Syndrome; Megdhel 3-Methylglutaconic Aciduria, Type VI; MGCA6, Datasheet [online], OMIM, Creation date: Jul. 2012 [retrieved on Aug. 27, 2024]. Retrieved from the Internet: <URL:https://www.omim.org/entry/614739#:~:text=on%20chromosome%206q25.-,Description, excretion%20of%203%2Dmethylglutaconic%20acid.>, 3 pages.

Alfred et al., "Microglial activation and inflammatory response in a mouse model of Leber's Hereditary Optic Neuropathy," Investigative Ophthalmology & Visual Science. Apr. 30, 2014;55(13):1352.

Ataxia Neuropathy Spectrum, Datasheet [online], MedlinePlus, Last Updated: Jun. 2011 [retrieved on Aug. 27, 2024]. Retrieved from the Internet:<URL:https://medlineplus.gov/genetics/condition/ataxia-neuropathy-spectrum/#causes>, 2 pages.

Atorino et al., "Loss of m-AAA protease in mitochondria causes complex I deficiency and increased sensitivity to oxidative stress in hereditary spastic paraplegia," The Journal of cell biology. Nov. 24, 2003;163(4):777-87.

Ball et al., "Mitochondrial DNA-•Associated Leigh Syndrome Spectrum," Oct. 30, 2003 [Updated May 9, 2024]. In: Adam MP, Feldman J, Mirzaa GM, et al., editors. GeneReviews® [Internet]. Seattle (WA): University of Washington, Seattle; 1993-2024, 37 pages.

Cohen et al., "POLG-Related Disorders," Mar. 16, 2010 [Updated Feb. 29, 2024]. In: Adam MP, Feldman J, Mirzaa GM, et al., editors. GeneReviews® [Internet]. Seattle (WA): University of Washington, Seattle; 1993-2024, 38 pages.

Complex I Deficiency, Datasheet [online], United Mitochondrial Disease Foundation, 2023 [retrieved on Jul. 24, 2024]. Retrieved from the Internet:<URL:https://www.umdf.org/complex-i-deficiency/>, 5 pages.

Goldstein et al., "Single Large-Scale Mitochondrial DNA Deletion Syndromes," Dec. 17, 2003 [Updated Sep. 28, 2023]. In: Adam MP, Feldman J, Mirzaa GM, et al., editors. GeneReviews® [Internet]. Seattle (WA): University of Washington, Seattle; 1993-2024, 27 pages.

Khambatta et al., "Kearns-Sayre syndrome: a case series of 35 adults and children," International journal of general medicine. Jul. 3, 2014:325-32.

Lopriore et al., "Mitochondrial ataxias: molecular classification and clinical heterogeneity," Neurology International. Apr. 2, 2022;14(2):337-56.

Majamaa et al., "Metabolic interventions against complex I deficiency in MELAS syndrome," Molecular and cellular biochemistry. Sep. 1997;174:291-6.

Park et al., "Molecular diagnosis of myoclonus epilepsy associated with ragged-red fibers syndrome in the absence of ragged red fibers," Frontiers in Neurology. Sep. 29, 2017;8:1-4.

Rotig et al., "Spectrum of mitochondrial DNA rearrangements in the Pearson marrow-pancreas syndrome," Human molecular genetics. Aug. 1, 1995;4(8):1327-30.

Ruhoy et al., "The genetics of Leigh syndrome and its implications for clinical practice and risk management," The application of clinical genetics. Nov. 13, 2014:221-34.

Saneto et al., "Alpers-huttenlocher syndrome: A review," Pediatric Neurology. Mar. 1, 2013;48(3):167-78.

(56) References Cited

OTHER PUBLICATIONS

Shoffner et al., "Spontaneous Kearns-Sayre/chronic external ophthalmoplegia plus syndrome associated with a mitochondrial DNA deletion: a slip-replication model and metabolic therapy," Proceedings of the National Academy of Sciences. Oct. 1989;86(20):7952-6.

Smith et al., "Astrocytic pathology in Alpers' syndrome," Acta Neuropathologica Communications. May 31, 2023;11(1):1-13.

Mssing et al., "Multiple mtDNA deletions with features of MNGIE," Neurology. Sep. 24, 2002;59(6):926-9.

Wiltshire et al., "Juvenile Alpers disease," Archives of neurology. Jan. 1, 2008;65(1):121-4.

Yu et al., "Mitochondrial complex I subunit deficiency promotes pancreatic α-cell proliferation," Molecular Metabolism. Jun. 1, 2022;60:1-10.

\* cited by examiner

CANNABIDIOL AND/OR DERIVATIVES THEREOF FOR USE IN THE TREATMENT OF MITOCHONDRIAL DISEASES

CROSS REFERENCE TO RELATED APPLICATIONS

This is a U.S. National Phase application claiming priority to PCT/EP2020/051772, filed Jan. 24, 2020, the entire contents of which are hereby expressly incorporated by reference in its entirety including, without limitation, the specification, claims, and abstract, as well as any figures, tables, or drawings thereof.

FIELD OF THE INVENTION

The invention relates to the use of cannabidiol (CBD) and/or a derivative thereof, in the treatment of mitochondrial diseases. In certain preferred embodiments, the CBD, and/or a derivative thereof is substantially devoid of tetrahydrocannabinol (THC). Moreover, the present invention also relates to a composition comprising the CBD and/or a derivative thereof and to a method of treating mitochondrial diseases in a subject, comprising administering to the subject in need thereof a therapeutically effective amount of the CBD, a derivative thereof and/or a composition comprising thereof.

BACKGROUND OF THE INVENTION

Cellular activity requires high energetic support provided by mitochondria, the cell organelles producing ATP through respiration and regulating cellular metabolism. Deficits in mitochondrial function can lead to a heterogeneous group of severe, and usually fatal, pathologies known as mitochondrial diseases (MD). Among mitochondrial diseases, those designated as primary mitochondrial diseases (PMD), affect 1:5,000 individuals, and are caused by mutations in either nuclear or mitochondrial genomes. These mutations generally give rise to a primary dysfunction of the respiratory chain, with a decreased enzyme function in one or more of the five respiratory complexes and the concomitant deficiency in ATP synthesis. Some examples of primary mitochondrial diseases are mitochondrial encephalopathy, lactic acidosis, and stroke-like episodes (MELAS), Leigh syndrome, Leber's hereditary optic neuropathy (LHON), myoclonic epilepsy with ragged-red fibers (MERRF), neurogenic weakness, ataxia, and retinitis pigmentosa (NARP), Kearns-Sayre syndrome, and Pearson's syndrome.

Despite the diverse signature traits that can be observed in PMD, in general, those cells and organs that require the most energy are the ones primarily affected. These include the CNS—with clinical features involving both the brain and spinal cord—, the heart, the muscle, and the gastrointestinal tract. PMD involving the CNS may display a large variety of symptoms such as neurodegeneration, seizures, myoclonus, myopathy, ataxia, stroke-like episodes, cognitive decline, migraine, atypical cerebral palsy, optic atrophy, and autism. Signs of neuroinflammation also represent a common pathological finding in PMD. Additionally, neuroimaging studies often reveal basal ganglia necrosis, stroke lesions, calcification, and leukodystrophy in certain PMD. Affected peripheral nerves can lead to neuropathic pain, absent reflexes, and dysautonomia, among others.

The contribution of mitochondrial dysfunction to human disease was already recognised in the late 1980s, when maternally inherited point mutations, as well as deletions arising spontaneously during development, were found to be associated with rare neurological syndromes. Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Leber's Hereditary Optic Neuropathy (LHON), dominant optic atrophy (DOA); mitochondrial myopathy, encephalopathy, lactacidosis, and stroke (MELAS), Myoclonus Epilepsy Associated with Ragged-Red Fibers (MERRF) syndrome, Leigh syndrome, and oxidative phosphorylation disorders. Most mitochondrial diseases involve children who manifest the signs and symptoms of accelerated aging, including neurodegenerative diseases, stroke, blindness, hearing impairment, diabetes, and heart failure.

Very few treatments are available for patients suffering from these mitochondrial diseases. Most of them are often supportive and palliative, and include vitamin supplements (Parikh, S., et al. Curr. Treat. Options Neurol. 2009, 11, 414-430), cofactors, nutritional diets (Pfeffer, G., et al. Cochrane Database Syst. Rev. 2012, CD004426), and exercise therapy (Cejudo, P., et al. Muscle Nerve. 2005, 32, 342-350; Jeppesen, T. D., et al. Brain J. Neurol. 2006, 129, 3402-3412; Taivassalo, T., et al. Brain J. Neurol. 2006, 129, 3391-3401). Despite their safety and high tolerability, the efficacy of these supplements is still limited. The main problem with the most of these supplements is that either they have not been tested in double-blind randomized trials, or those that have been tested showed no better response than placebo. The same argument is applied for some synthetic agents such as idebenone, EPI-743, and dichloroacetate. Another drawback of known treatments is that they often address the symptomatology of the diseases without improving the altered enzyme function of one or more of the five respiratory complexes and the concomitant deficiency in ATP synthesis underlying the diseases.

WO 2012/019032 discloses methods of treatment, prevention, or suppression of symptoms associated with a mitochondrial disorder and/or modulating, normalizing, or enhancing one or more energy biomarkers, whereby vitamin K analogues are administered. WO 2012/019029 discloses methods of treatment, prevention, or suppression of symptoms associated with a mitochondrial disorder and/or modulating, normalizing, or enhancing one or more energy biomarkers, whereby naphtoquinones and derivatives thereof are administered. Distelmaier et al. (Antioxid Redox Signal. 2012; 17 (12): 1657-69) disclose that Trolox™ (6-hydroxy-2,5,7,8-tetramethylchroman-2-carboxylic acid), a water-soluble analogue of vitamin E, reduces the levels of ROS, increased mitofusins-mediated mitochondrial filamentation and expression of mitochondrial complex I, activity of citrate synthase and OXPHOS enzymes and cellular $O_2$ consumption in cultured healthy human skin fibroblasts. Moreover, WO 2014/011047 discloses methods for treating or preventing mitochondrial disorders, conditions associated with mitochondrial dysfunction and/or neoplastic diseases, using Trolox-derivatives. In particular, these derivatives can be used in modulating mitochondrial morphology and/or expression of OXPHOS enzymes and/or cellular ROS.

Moreover, the bezafibrate, an agonist of the peroxisome proliferator-activated receptor (PPAR), the AICAR, an adenosine monophosphate analogue that activates AMPK, and the vitamin B3 nicotinamide riboside have all been shown to boost mitochondrial biogenesis and improve muscle metabolism in mitochondrial myopathy mouse models (Yatsuga, S., and Suomalainen, A. Hum. Mol. Genet. 2012; 21: 526-535; Viscomi, C., et al. Cell Metab. 2011; 14: 80-90; Khan, N. A., et al. EMBO Mol. Med. 2014; 6: 721-731). Pharmacological activation of either PPARγ coactivator 1α (PGC-1α), which is considered the master regulator of mitochondrial biogenesis, or sirtuins, which act as metabolic sensors, has also shown encouraging results in mice (Komen, J. C., and Thorburn, D. R. Br. J. Pharmacol. 2014; 171: 1818-1836.). On the other hand, the antioxidant N-acetyl cysteine amide and the mTORC1 inhibitor rapamycin have been shown to improve brain disease in a mouse model of Leigh syndrome (Johnson, S. C., et al. Science. 2013; 342: 1524-1528; Liu, L., Cell. 2015; 160: 177-190).

Besides the abovementioned treatments, which are primarily antioxidants or agents modulating metabolic enzymes, other putative treatments for PMD include (i) gene therapy to reduce mutant mtDNA, (ii) mitochondria-targeted peptides and lipophilic cations for in vivo delivery of antioxidants or other drugs, (iii) modulation of mitochondrial dynamics, and (iv) allotopic expression of recoded wild-type mitochondrial genes (Leitao-Rocha, A., et al. Curr. Med. Chem. 2015; 22: 2458-2467).

Despite these encouraging preclinical data, controlled clinical trials are required to prove the efficacy of these agents in humans and the transfer of preclinical studies into clinics is not always linear and rapid. In this sense, several registered treatments for PMD are currently in clinical trials (https://clinicaltrials.gov). Some compounds that are currently being tested for their antioxidant properties include the para-benzoquinone analogue EPI-743, the derivative of the antioxidant KH176, and the triterpenoid compound RTA408. The coenzyme Q10—an essential component of the electron transport chain- and its analogue idebenone are also both being tested for their antioxidant properties. RP103 (cysteamine bitartrate), which improves redox imbalance by increasing intracellular glutathione, is also being tested in inherited MD. Alternatively, some ongoing clinical trials are using an adeno-associated viral vector to allotopically express the wild-type mitochondrial Nd4 gene in LHON subjects. Of note, none or scarce preclinical data supports these ongoing clinical trials and large-scale studies are needed to further assess the efficacy of these compounds in alleviating MD symptomatology.

There is however still a need in the art for new therapeutics and effective strategies to treat mitochondrial diseases, in particular diseases where mitochondria are impaired due to a dysfunctionality of the mitochondrial electron transport chain, for example a dysfunctionality of complex I.

SUMMARY OF THE INVENTION

It has been now surprisingly found that the administration of a cannabidiol compound to subjects suffering from mitochondrial diseases results particularly efficient for extended the life span observed in a mouse model of PMD, specifically in a mouse model of Leigh syndrome, which is the most common infantile PMD. In the mouse model of PMD used by the inventors mitochondria become impaired or dysfunctional due to the lacking Ndufs4 either in all cells or in GABAergic cells. As Ndufs4 encodes a protein involved in assembly, stability, and activity of complex I of the mitochondrial electron transport chain, when said protein is absent, complex I becomes dysfunctional and so do mitochondria.

Particularly, the inventors have found that the administration of CBD significantly delays the appearance of impaired motor skills, the neurological decline, and ultimately the early death observed in the mouse model of Leigh syndrome, as it is shown in the present invention (See Example 1).

These results are all the most surprising as it had previously been reported that CBD is capable of causing mitochondrial damages by inducing dissipation of the mitochondrial transmembrane potential, opening the mitochondrial permeability transition pore (mPTP), inducing overproduction of reactive oxygen species (ROS) and triggering an intrinsic apoptotic pathway (Olivas-Aguirre, M., et al. Cell Death and Disease. 2019; 10: 779)

In summary, the results of the present disclosure allow new therapeutic approaches to mitochondrial diseases to be developed, through the use of a cannabidiol compound and/or its derivates and pharmaceutical compositions comprising thereof. Therefore, one aspect of the invention relates to the use of a compound of Formula I for the treatment of mitochondrial diseases, in particular a disease selected from the group consisting of mitochondrial disease is selected from the group consisting of Mitochondrial Encephalopathy, Lactic Acidosis and Stroke-like episodes (MELAS), Leigh syndrome (LS), 3-Methylglutaconic aciduria with Deafness, Encephalopathy and Leigh-like syndrome (MEGDEL), Leber's Hereditary Optic Neuropathy (LHON), Myoclonic Epilepsy with Ragged-Red Fibers (MERRF), Maternally Inherited Leigh Syndrome (MILS), Ataxia Neuropathy spectrum, Hereditary Spastic Paraplegia (HSP), Neuropathy, Ataxia and Retinitis Pigmentosa (NARP), Kearns-Sayre syndrome (KSS), Pearson's syndrome, Maternally Inherited Diabetes and Deafness (MI DD), Mitochondrial Neuro-Gastro-Intestinal Encephalopathy (MNGIE), Mitochondrial Depletion Syndrome (MDS) and Alpers-Hutennlocher syndrome.

It should be appreciated that in the context of the present invention the terms "Cannabidiol compound", "cannabidiol" or "CBD" (which may be used interchangeably unless the context clearly dictates otherwise) refer to natural, semisynthetic or synthetic cannabinoid compound of formula (I). These compounds are not endogenous agonists (endocannabinoids) of the cannabinoid receptors CB 1 or CB2.

According to a first aspect, the invention relates to a compound of Formula (I):

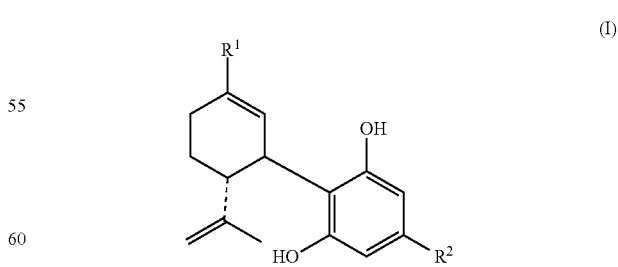

wherein:
R$^1$ is selected from (C$_1$-C$_5$)alkyl, —COOH and —CH$_2$OH; and
R$^2$ is selected from (C$_5$-C$_{12}$)alkyl, —OR$^3$ and —(CH$_2$)$_n$—O—(C$_1$-C$_5$)alkyl;

and wherein:
R³ is selected from (C₅-C₉)alkyl or (C₅-C₉)alkyl substituted at the terminal carbon atom by a phenyl group; and
n is an integer from 1 to 7,
for use in the treatment of mitochondrial diseases.

The term "alkyl", as used herein, alone or as part of another group, relates to saturated hydrocarbonated chains, both linear and branched, containing the number of carbon atoms indicated in each case throughout the present document and bound to the rest of the molecules through a single bond. Examples of alkyl groups are methyl, ethyl, n-propyl, isopropyl, n-butyl, isobutyl, terc-butyl, pentyl, hexyl, isohexyl, heptyl, 4,4-dimethylpentyl, octyl, 2,2,4-trimethylpentyl, nonyl, decyl, dodecyl and their different branched chain isomers. The alkyl groups may be optionally substituted by a phenyl group as indicated in each case throughout the present document.

In one preferred embodiment, $R_1$ is $(C_1-C_5)$alkyl and $R_2$ is $(C_5-C_{12})$alkyl.

In one more preferred embodiment, $R^1$ is $CH_3$ and $R^2$ is a straight alkyl having 5 carbon atoms (i.e. pentyl or $-C_5H_{11}$).

In another preferred embodiment, the compound of Formula (I) is cannabidiol. Cannabidiol has the following Formula (II):

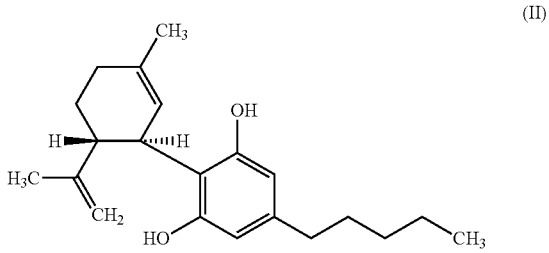 [SMILES: C=C(C)[C@@H]1CCC(C)=C[C@H]1c1c(O)cc(CCCCC)cc1O]

(II)

Thus, in another preferred embodiment, the invention refers to the CBD having the Formula (II), for use in the treatment of mitochondrial diseases.

Cannabidiol, CBD, (−)-trans-2-p-mentha-1,8-dien-3-yl-5-pentylresorcinol, is one of many cannabinoids that naturally occur in *cannabis*. CBD is a constituent of *Cannabis* species, such as the hemp plant (*Cannabis sativa*), having no psychotropic effects, as opposed to THC. CBD does not induce psychoactive or cognitive effects and is well tolerated by humans without significant adverse effects. Unlike THC, cannabidiol binds very weakly to CB1 and CB2 receptors. Synthetic cannabidiol has the same structure as naturally occurring cannabidiol. Commercially available cannabidiol usually contains THC although there is also synthetic cannabidiol. In this sense, synthetic cannabidiol may be prepared without contaminating THC. Synthesized cannabidiol may be purified to a purity of greater than 98%. The level of purity may be determined by chromatography. In a preferably embodiment of the present invention, the cannabidiol has a purity greater than 99%, more preferably, the cannabidiol has a purity greater than 99.5%, more preferably a purity of 99.9%. In certain more preferred embodiments, the CBD, and/or a derivative thereof is substantially devoid of THC. In particular, the CBD may be a synthetically produced CBD without any trace of THC.

The compounds of the present invention represented by the general Formula (I) may include its pharmaceutically acceptable salts, hydrates or stereoisomers.

As used herein, the term "derivative(s)" relates to the compound of Formula (I) or a stereoisomer thereof means organic molecules that are structurally closely related to the compound of Formula (I) or a stereoisomer itself and that have similar characteristics and therapeutic effects, preferably as a therapeutic compound for use in the treatment of MD.

As used herein, the term "stereoisomer(s)" as it relates to the compound of Formula (I) means any possible enantiomers, diastereomers, cis-trans-isomers and/or E-/Z-isomers of the compound of Formula (I) or its salts or its hydrates. In particular, the term "stereoisomer" means a single compound or a mixture of two or more compounds, wherein at least one chiral center is predominantly present in one definite isomeric form. It is also possible that two or more stereogenic centers are predominantly present in one definite isomeric form. In the sense of the present invention, "predominantly" has the meaning of at least 60%, preferably at least 70%, particularly preferably at least 80%, most preferably at least 90%. According to the present invention, also stereoisomers of the compound of Formula (I) or a derivative thereof may be present as a salt or a hydrate.

As used herein, the term "salt(s)" as it relates to the compound of Formula (I) means the physiologically acceptable acid addition salts and base salts of the compound of Formula (I). Suitable acid addition salts are formed from acids which form non-toxic salts. Examples include but are not limited to the acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride/chloride, hydrobromide, bromide, hydroiodide, iodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, saccharate, stearate, succinate, tartrate, tosylate and trifluoroacetate salts. Suitable base salts are formed from bases which form non-toxic salts. Examples include but are not limited to the aluminium, arginine, benzathine, calcium, choline, diethyl amine, diolamine, glycine, lysine, magnesium, meglumine, olamine, potassium, sodium, tromethamine and zinc salts.

As used herein, the term "hydrate(s)" as it relates to the compound of Formula (I) means the compound of Formula (I) or a derivative or a stereoisomer or a salt thereof that include water. "Hydrate(s)" are formed by the addition of water or its elements. In one embodiment, the compound of Formula (I) or a stereoisomer or a salt thereof may form crystals that incorporate water into the crystalline structure without chemical alteration. The terms stereoisomer, salt, and hydrate may also be used in conjunction with one another. For example, a compound of Formula (I) may have a stereoisomer and/or a salt. Similarly, a stereoisomer of the compound of Formula (I) may have a salt. Combinations of these terms are considered to be within the scope of the invention.

For the purposes of the present invention, the terms "treat", "treatment" or "treating" refer to an intervention performed with the intention of preventing the development or combating the effects caused as a consequence of the disease or pathological condition of interest in a subject. Thus, these terms including:

i. inhibit the disease or pathological condition, i.e. stop the development thereof;
ii. alleviate the disease or pathological condition, i.e. cause the regression of the disease or pathological condition or its symptomatology; and
iii. stabilize the disease or pathological condition.

Moreover, "treatment" refers both to therapeutic treatment as well as to prophylactic or preventative measures.

As used herein, the term "mitochondrial disease", "mitochondrial disorder" or "MD" used interchangeably thorough of the present disclosure, refer to a primary mitochondrial disease, i.e. a disease, disorder, or condition in which the function of subject's mitochondria become impaired or dysfunctional. Examples of primary mitochondrial diseases that may be treated with the compound or method described herein include Mitochondrial Encephalopathy, Lactic Acidosis and Stroke-like episodes (MELAS), Leigh syndrome (LS), 3-Methylglutaconic aciduria with Deafness, Encephalopathy and Leigh-like syndrome (MEGDEL), Leber's Hereditary Optic Neuropathy (LHON), Myoclonic Epilepsy with Ragged-Red Fibers (MERRF), Maternally Inherited Leigh Syndrome (MILS), Ataxia Neuropathy spectrum, Hereditary Spastic Paraplegia (HSP), Neuropathy, Ataxia and Retinitis Pigmentosa (NARP), Kearns-Sayre syndrome (KSS), Pearson's syndrome, Maternally Inherited Diabetes and Deafness (MIDD), Mitochondrial Neuro-Gastro-Intestinal Encephalopathy (MNGIE), Mitochondrial Depletion Syndrome (MDS) and Alpers-Huttenlocher syndrome.

Mitochondrial Encephalopathy, Lactic Acidosis and Stroke-like episodes (MELAS) is a genetically heterogeneous mitochondrial disorder with a variable clinical phenotype. The disorder is accompanied by features of central nervous system involvement, including seizures, hemiparesis, hemianopsia, cortical blindness, and episodic vomiting (https://omim.org/entry/540000 and Pavlakis et al., 1984; Montagna et al., 1988).

Leigh syndrome (LS) is a clinically and genetically heterogeneous disorder resulting from defective mitochondrial energy generation. It most commonly presents as a progressive and severe neurodegenerative disorder with onset within the first months or years of life, and may result in early death. Affected individuals usually show global developmental delay or developmental regression, hypotonia, ataxia, dystonia, and ophthalmologic abnormalities, such as nystagmus or optic atrophy (https://omim.org/entry/256000 and Lake et al., 2015).

3-Methylglutaconic aciduria with Deafness, Encephalopathy and Leigh-like syndrome (MEGDEL) is an autosomal recessive disorder characterized by childhood onset of delayed psychomotor development or psychomotor regression, sensorineural deafness, spasticity or dystonia, and increased excretion of 3-methylglutaconic acid. Brain imaging shows cerebral and cerebellar atrophy as well as lesions in the basal ganglia reminiscent of Leigh syndrome (https://omim.orq/entry/614739 and Maas et al., 2017).

Leber's Hereditary Optic Neuropathy (LHON) presents in midlife as acute or subacute central vision loss leading to central scotoma and blindness. The disease has been associated with many missense mutations in the mtDNA (mitochondrial DNA) that can act autonomously or in association with each other to cause the disease (https://omim.orq/entry/535000 and Yu-Wai-Man et al. (2009)).

Myoclonic Epilepsy with Ragged-Red Fibers (MERRF) represents a phenotype that can be produced by mutation in more than one mitochondrial gene, e.g., MTTK, MTTL1, MTTH, MTTS1, MTTS2, MTTF. Features of the MERRF syndrome have also been associated with mutation in the MTND5 gene (https://omim.org/entry/545000). A specific mutation in mitochondrial gene MTKK was first demonstrated by Shoffner et al. (1990). The A-to-G mutation at nucleotide 8344 accounts for 80 to 90% of MERRF cases (Shoffner and Wallace, 1992). Biochemically, the mutation produces multiple deficiencies in the enzyme complexes of the respiratory chain, most prominently involving NADH-CoQ reductase (complex I) in cytochrome c oxidase (COX) (complex IV), consistent with a defect in translation of all mtDNA-encoded genes.

Maternally Inherited Leigh Syndrome (MILS) is a rare subtype of Leigh syndrome with clinical characteristics of encephalopathy, lactic acidosis, seizures, cardiomyopathy, respiratory disorders and developmental delay. Onset in infancy or early childhood resulting from maternally-inherited mutations in mitochondrial DNA (https://www.ncbi.nlm.nih.gov/medgen/443976).

Ataxia Neuropathy spectrum includes the phenotypes previously referred to as mitochondrial recessive ataxia syndrome (MIRAS) and sensory ataxia neuropathy dysarthria and ophthalmoplegia (SANDO). About 90% of persons in the ANS have ataxia and neuropathy as core features. Approximately two thirds develop seizures and almost one half develop ophthalmoplegia; clinical myopathy is rare (https://www.ncbi.nlm.nih.gov/books/NBK26471/). ANS includes mitochondrial recessive ataxia syndrome (MIRAS) and a separate entity known as sensory ataxia neuropathy dysarthria and ophthalmoplegia (SANDO) (Fadic et al 1997).

The predominant signs and symptoms of hereditary spastic paraplegia (HSP) are lower-extremity weakness and spasticity. Spastic paraplegia 7 (a type of HSP) is an autosomal recessive disorder caused by mutations in the gene encoding paraplegin, a protein located at the inner mitochondrial membrane and involved in the processing of other mitochondrial proteins (Wedding et al. 2014).

Neuropathy, Ataxia and Retinitis Pigmentosa (NARP) is caused by mutation in the gene encoding subunit 6 of mitochondrial H(+)-ATPase (https://omim.org/entry/551500). It is a rare disease with mitochondrial inheritance that causes a variety of signs and symptoms chiefly affecting the nervous system Beginning in childhood or early adulthood, most people with NARP experience numbness, tingling, or pain in the arms and legs (sensory neuropathy); muscle weakness; and problems with balance and coordination (ataxia). Many affected individuals also have vision loss caused by changes in the light-sensitive tissue that lines the back of the eye (the retina). In some cases, the vision loss results from a condition called retinitis pigmentosa. This eye disease causes the light-sensing cells of the retina gradually to deteriorate (https://en.wikipedia.org/wiki/Neuropathy,_ataxia,_and_retinitis_pigmentosa).

Kearns-Sayre syndrome (KSS) is caused by various mitochondrial deletions. It is inherited in an autosomal recessive manner and is a mitochondrial myopathy with a typical onset before 20 years of age. KSS is a more severe syndromic variant of chronic progressive external ophthalmoplegia (abbreviated CPEO), a syndrome that is characterized by isolated involvement of the muscles controlling movement of the eyelid (levator palpebrae, orbicularis oculi) and eye (extra-ocular muscles). This results in ptosis and ophthalmoplegia respectively. KSS involves a combination of the already described CPEO as well as pigmentary retinopathy in both eyes and cardiac conduction abnormalities. Other symptoms may include cerebellar ataxia, proximal muscle weakness, deafness, diabetes mellitus, growth hormone deficiency, hypoparathyroidism, and other endocrinopathies. (en.wikipedia.org/wiki/Kearns-Sayre_syndrome and https://omim.org/entry/530000).

Pearson's syndrome (also known as Pearson marrow-pancreas syndrome) is a contiguous gene deletion/duplication syndrome involving several mtDNA genes, it involves refractory sideroblastic anemia with vacuolization of marrow precursors and exocrine pancreatic dysfunction (https://omim.org/entry/557000).

Maternally Inherited Diabetes and Deafness (MIDD) is a mitochondrial disorder characterized by onset of sensorineural hearing loss and diabetes in adulthood. Some patients may have additional features observed in mitochondrial disorders, including pigmentary retinopathy, ptosis, cardiomyopathy, myopathy, renal problems, and neuropsychiatric symptoms (Ballinger et al., 1992; Reardon et al., 1992; Guillausseau et al., 2001) which can be caused by mutation in several mitochondrial genes, including MTTL1, MTTE and MTTK (https://omim.org/entry/520000).

Mitochondrial Neuro-Gastro-Intestinal Encephalopathy (MNGIE) manifests as a neurogastrointestinal encephalopathy and is caused by homozygous or compound heterozygous mutation in the nuclear-encoded thymidine phosphorylase gene (TYMP; 131222) on chromosome 22q13. Papadimitriou et al. (1998) examined skeletal muscle of subjects, including a pair of monozygotic twins, with MNGIE and found that all showed ragged-red and cytochrome c oxidase (COX)-negative fibers, as well as partial deficiency of complexes I and IV.

Mitochondrial DNA Depletion Syndrome (MDS) is caused by a single large-scale deletion in the mtDNA genome (https://www.ncbi.nlm.nih.gov/books/NBK1203/).

Alpers-Huttenlocher syndrome is caused by homozygous or compound heterozygous mutation in the nuclear gene encoding mitochondrial DNA polymerase gamma (POLG; 174763) on chromosome 15q26 (https://omim.org/entry/203700). It is an autosomal recessive disorder characterized by a clinical triad of psychomotor retardation, intractable epilepsy, and liver failure in infants and young children. Pathologic findings include neuronal loss in the cerebral gray matter with reactive astrocytosis and liver cirrhosis. The disorder is progressive and often leads to death from hepatic failure or status epilepticus before age 3 years (Milone and Massie, 2010)

In an embodiment, the mitochondrial disease is selected from the group consisting of Mitochondrial Encephalopathy, Lactic Acidosis and Stroke-like episodes (MELAS), Leigh syndrome (LS), 3-Methylglutaconic aciduria with Deafness, Encephalopathy and Leigh-like syndrome (MEGDEL), Leber's Hereditary Optic Neuropathy (LHON), Myoclonic Epilepsy with Ragged-Red Fibers (MERRF), Maternally Inherited Leigh Syndrome (MILS), Ataxia Neuropathy spectrum, Hereditary Spastic Paraplegia (HSP), Neuropathy, Ataxia and Retinitis Pigmentosa (NARP), Kearns-Sayre syndrome (KSS), Pearson's syndrome, Maternally Inherited Diabetes and Deafness (MI DD), Mitochondrial Neuro-Gastro-Intestinal Encephalopathy (MNGIE) and Mitochondrial Depletion Syndrome (MDS).

In another embodiment the mitochondrial disease is selected from the group consisting of Mitochondrial Encephalopathy, Lactic Acidosis and Stroke-like episodes (MELAS), Leigh syndrome (LS), 3-Methylglutaconic aciduria with Deafness, Encephalopathy and Leigh-like syndrome (MEGDEL), Leber's Hereditary Optic Neuropathy (LHON), Myoclonic Epilepsy with Ragged-Red Fibers (MERRF), Kearns-Sayre syndrome (KSS), Mitochondrial Neuro-Gastro-Intestinal Encephalopathy (MNGIE) and Alpers-Huttenlocher syndrome.

In another embodiment the mitochondrial disease is selected from the group consisting of Mitochondrial Encephalopathy, Lactic Acidosis and Stroke-like episodes (MELAS), Leigh syndrome (LS), 3-Methylglutaconic aciduria with Deafness, Encephalopathy and Leigh-like syndrome (MEGDEL), Leber's Hereditary Optic Neuropathy (LHON), Myoclonic Epilepsy with Ragged-Red Fibers (MERRF), Kearns-Sayre syndrome (KSS) and Mitochondrial Neuro-Gastro-Intestinal Encephalopathy (MNGIE).

In another embodiment the mitochondrial disease is Alpers-Huttenlocher syndrome.

In a preferred embodiment, the mitochondrial disease is Leigh syndrome.

The compounds of Formula (I), preferably the CBD of Formula (II) for use in the instant invention may be used in combination with at least one additional pharmaceutical active ingredient, for example, idebenone or any derivative or analogues thereof, antioxidants and mixtures thereof.

In a preferred embodiment the analogues of idebenone are selected from the list consisting of ubiquinol and ubiquinone, among others. In another preferred embodiments as antioxidant could be selected the vitamin C, E or combinations thereof.

In a second aspect, the invention provides a pharmaceutical composition comprising a therapeutically effective amount of a compound as defined in the first aspect and a physiologically acceptable carrier or excipient, for use in the treatment of mitochondrial diseases.

In a third aspect, the present invention provides the use of a compound as defined in the first aspect for the preparation of a medicament for the treatment of mitochondrial diseases.

In a fourth aspect, the present invention provides a method of treatment or prevention of a mitochondrial disease by administration of a compound as defined in the first aspect to a patient in need thereof.

In an embodiment of any of aspects 1 to 4 described above the compounds of Formula (I), preferably the CBD of Formula (II), may be used with a further pharmaceutical active ingredient. When the compound of the invention is used in combination with other pharmaceutical active ingredients, the compounds may be administered either sequentially or simultaneously by any convenient route. The combinations referred to above may conveniently be presented for use in the form of a pharmaceutical compositions and thus pharmaceutical compositions comprising a combination as defined above optimally together with a pharmaceutically acceptable carrier or excipient comprise a further aspect of the invention. The individual components of such combinations may be administered either sequentially or simultaneously in separate or combined pharmaceutical compositions.

In a further embodiment of any of aspects 1 to 4 described above the compound of formula (I) is used in the absence of tetrahydrocannabinol (THC).

Thus, the invention also provides a pharmaceutical composition comprising a therapeutically effective amount of the compound of the invention as active ingredient, and a physiologically acceptable carrier or excipient, for use in the treatment of mitochondrial diseases.

In this specification, the term "pharmaceutical composition" refers to any substance used for the alleviation, treatment or cure of a disease in a human being or in animals. The pharmaceutical composition of the invention can be used alone or in combination with other pharmaceutical compositions. In a preferred embodiment, the pharmaceutical composition further comprises a pharmaceutically acceptable carrier or excipient.

In a preferred embodiment, the pharmaceutical composition further comprises at least one additional pharmaceutical active ingredient other than the compound having Formula I, and with the proviso that if the additional pharmaceutical active ingredient is THC, it comprises lower than 5% (v/v)

of the composition, more preferably the pharmaceutical composition of the invention does not comprise THC.

By "active pharmaceutical ingredient" means any compound or substance whose administration has a therapeutic effect or a positive effect on health or general condition of a patient or a subject which it is administered. According to the present invention, the active pharmaceutical ingredient relates to the compounds of Formula I, preferably the CBD of Formula (II). Moreover, an additional active pharmaceutical ingredient may be active against mitochondrial diseases.

Examples of additional active pharmaceutical ingredients that may be present in the composition of the present invention include, without limitation, Idebenone and its analogues, ubiquinol/ubiquinone, antioxidants such as vitamin C or E.

The term "excipient" refers to a substance which helps the absorption of the pharmaceutical composition, comprising the compound of the invention, stabilizes said pharmaceutical composition or helps in the manufacture thereof in the sense of giving it consistency, form, flavour or any other specific functional characteristic. Thus, excipients could have the function of keeping the ingredients bound together, such as for example starches, sugars or celluloses, a sweetening function, a colorant function, a protection function, such as for example isolating it from the air and/or moisture, a filler function for a tablet, capsule or any other form of formulation, such as for example dibasic calcium phosphate, a disintegrating function to facilitate the dissolution of the components and their absorption, without excluding other types of excipients not mentioned in this paragraph.

A "pharmaceutically acceptable carrier" (or "pharmacologically acceptable") refers to any substance, or combination of substances, known in the pharmaceutical sector, used in the manufacture of pharmaceutical forms of administration and includes, but is not limited to, solids, liquids, solvents or surfactants. The carrier can be an inert substance or have a similar action to any of the compounds of the present invention, having the function of facilitating the incorporation of the drug as well as other compounds, allowing for an improved dosage and administration or providing consistency and form to the pharmaceutical composition. When the dosage form is liquid, the carrier is the diluent. The term "pharmacologically acceptable" refers to the fact that the compound referred to is allowed and evaluated so that it does not cause harm to the organisms to which it is administered.

The pharmaceutical composition of this invention can be facilitated through any route of administration, and as such, said composition shall be formulated in the pharmaceutical form suitable to the selected route of administration. Thus, administration can be, for example, oral, topical, sublingual, ocular, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, or by inhalation. Suitable sites of administration include, but are not limited to, skin, muscle, gastrointestinal, eye, and ear. The compositions may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages. The compositions of the present disclosure can also be delivered as microspheres for slow release in the body or as nanoparticles.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. Proper formulation is dependent, inter alia, upon the route of administration chosen.

The pharmaceutical composition according to the present invention may be administered using any combination of dosage and route of administration effective to achieve the desired effect. Moreover, the components of the composition of the invention may also be administered either sequentially or simultaneously in separate or combined pharmaceutical compositions, in any order. When combined in the same composition it will be appreciated that the different compounds must be stable and compatible with each other and the other components of the formulation and may be formulated for administration. When formulated separately they may be provided in any convenient formulation, conveniently in such a manner as are known for such compounds in the art.

When the compound of the invention is used in combination with at least additional active pharmaceutical ingredients against the same disease, the dose of each compound may differ from that when the compound is used alone. Appropriate doses will be readily appreciated by those skilled in the art.

Any medicament having utility in an application described herein can be used in co-therapy, co-administration or co-formulation with the composition as described above. By "co-administer" it is meant that a composition described herein is administered at the same time, just prior to, or just after the administration of one or more additional therapies. The compound of the disclosure can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation). Furthermore, the invention also provides methods of treating mitochondrial diseases which comprises administering a therapeutically effective amount of the compound of Formula (I), or the pharmaceutical composition of the invention, to a subject in need thereof. In a more preferred embodiment, the method of treating mitochondrial diseases of the invention comprises administering a therapeutically effective amount of the CBD of Formula (II), or the pharmaceutical composition of the invention comprising the CBD of Formula (II), to a subject in need thereof.

For the purposes of the present invention, the term "therapeutically effective amount" refers to the amount of compound or composition of the invention required to achieve an appreciable improvement in the state, for example, a pathology, of the disease or condition which is the object of the treatment.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to provide a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In the present invention the terms "subject" and "individual" are used interchangeably. As used in the present document, the term "subject" or "individual" refers to all animals classified as mammals and includes, but is not limited to, farm and domestic animals, primates and humans, for example human beings, non-human primates, cows, horses, pigs, sheep, goats, dogs, cats or rodents. Preferably, the subject is a human being, male or female, of any age or race.

A "subject in need of treatment" includes any case in which said subject already has the disorder, as well as any case in which the disorder is to be prevented.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

EXAMPLES

Figure 1:
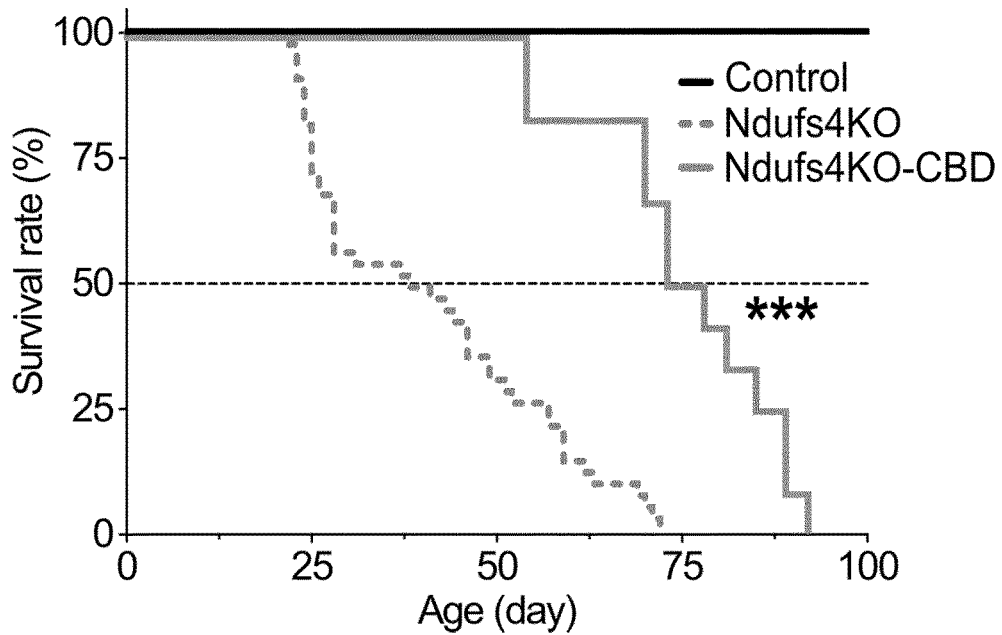
FIG. 1. Repeated CBD treatment improves survival in a mouse model of Leigh syndrome. Survival of the Ndufs4$^{-/-}$ mice was significantly extended by chronic CBD treatment (100 mg/kg, once daily) (log-rank $p<0.0001$). Control: wild-type (Ndufs4$^{+/+}$) mice; Ndufs4KO: Ndufs4$^{-/-}$ mice; Ndufs4KO-CBD: Ndufs4$^{-/-}$ mice treated with CBD.

The invention is illustrated below by means of tests carried out by the inventors which reveal the effectiveness of the product of the invention.

Materials and Methods

Animals

All animal experiments were performed with the approval of the ethical committee at Universitat Autònoma de Barcelona (CEEAH) and Generalitat de Catalunya (DMAH). Animals were housed under standardized conditions with a 12-h light/dark cycle, stable temperature (22±2° C.), controlled humidity (55±10%), and food and water ad libitum.

Two mouse lines were used in this study: (1) a validated mouse genetic model of MD (Kruse, S. E., et al. Cell Metab. 2008, 7: 312-320; Quintana, A., et al. Proc. Natl. Acad. Sci. USA. 2010, 107: 10996-11001), lacking Ndufs4 constitutively (Ndufs4$^{-/-}$, Ndufs4 KO) and wild-type (WT) littermates (Ndufs4$^{+/+}$) as controls, and (2) a conditional knock-out mouse line lacking Ndufs4 selectively in GABAergic cells (Bolea et al. 2019 (https://elifesciences.org/articles/47163). For the latter, mice expressing cre-recombinase under the control of the Gad2 promoter (Quintana, A., et al. Nat. Neurosci. 2012, 15: 1547-1555) and one floxed Ndufs4 allele (Gad2$^{cre/+}$:Ndufs4$^{lox/+}$) were bred with mice carrying two floxed Ndufs4 alleles (Ndufs4$^{lox/lox}$). Out of all the possible offspring, Gad2$^{cre/+}$: Ndufs4$^{lox/lox}$ mice bear Ndufs4 deficiency selectively in GABAergic neurons. Mice with Gad2$^{cre/+}$:Ndufs4$^{lox/+}$ genotype with one functional Ndufs4 allele as well as mice with the Gad2$^{cre/+}$:Ndufs4$^{lox/lox}$ genotype were used as controls.

Drugs and Treatments

Cannabidiol (CBD; 100 mg/kg) was purchased from THC Pharm-GmbH and cremophor-EL from Sigma-Aldrich. CBD was diluted in vehicle preparation containing 5% ethanol (vol/vol), 5% cremophor-EL (vol/vol), and 90% saline (vol/vol). CBD and vehicle solutions were administered intraperitoneally in a volume of 10 ml/kg and 30 min prior to the behavioural task.

Behavioural Assays

Mice were handled for 3 days prior to testing for habituation. Since there was no evidence of sex differences in our behavioural measurements, data from male and female mice were pooled. All experiments were blinded to genotype during behavioural testing.

Clasping

Clasping behaviour was used as a sign of neurological degeneration (Johnson, S. C., et al. Science. 2013, 342: 1524-1528). Clasping consisted in an inward curling of the spine and a retraction of the forelimbs and/or hindlimbs toward the midline of the body.

Rotarod

Rotarod was performed at postnatal day 30, 40, and 50. Mice were placed on a rotating drum that gradually accelerated from 4 rpm to 40 rpm over 300 sec. Each trial ended when a mouse fell off, made one complete backward revolution while hanging on, or reached 5-min. Each mouse was tested in 3 trials/day spaced 20 min apart. The results of the 3 trials were averaged.

Three-Chamber Social Approach

A three-chamber arena was used to assess sociability as previously described (Puighermanal et al, Front Mol Neurosci., 2017, 10:419). Briefly, on day 1, stranger target mice were habituated to the wire cups. On day 2, test mice were placed in the middle chamber and allowed to freely explore all the empty chambers of the apparatus for 10 min. Next, an unfamiliar mouse (age and gender matched) was introduced into one of the two side chambers, enclosed in a wire cage allowing only for the test mouse to initiate any social interaction. An identical empty wire cage was placed in the other side chamber. Following placement, the test mouse was allowed to explore the whole three-chamber arena for 10 min. The time spent sniffing the unfamiliar mouse and the empty wire cage was manually scored. The discrimination index for sociability was calculated as follows: (time exploring unfamiliar mouse—time exploring empty wire cage)/(total exploration time)*100. The test was performed around postnatal day 48.

Statistical Analyses

GraphPad Prism v6.0 software was used for statistical analyses. Data are shown as the means±SEM. All statistical analyses were performed using two-way analysis of variance (ANOVA) for multiple comparisons, followed by Tukey's post hoc test. Student t-test (unpaired, two-tailed) was used for groups of two, when relevant. *$p<0.05$, $p<0.01$ and *$p<0.001$.

Example 1. Efficacy of CBD in the Treatment of Mitochondrial Diseases, Exemplified in a Mouse Model of Leigh Syndrome The effects of CBD treatment (100 mg/kg, once/day, intraperitoneal) beginning a few days after weaning (postnatal day 24-30) in Ndufs4 knockout (Ndufs4$^{-/-}$) mice, a well characterized mouse model of a MD, were firstly examined.

Ndufs4 encodes a protein involved in assembly, stability, and activity of complex I of the mitochondrial electron transport chain. Ndufs4$^{-/-}$ mice display a progressive neurodegenerative phenotype, which resembles the human disease and includes retarded growth rate, weight loss, lethargy, loss of motor skills, and premature death. Strikingly, the inventors found that CBD administration significantly extended the life span of Ndufs4$^{-/-}$ mice (FIG. 1). In particular, the median survival of Ndufs4KO mice were 38 days whereas the one of Ndufs4KO mice treated with CBD (Ndufs4KO-CBD) was 75.5 days.

Figure 2:
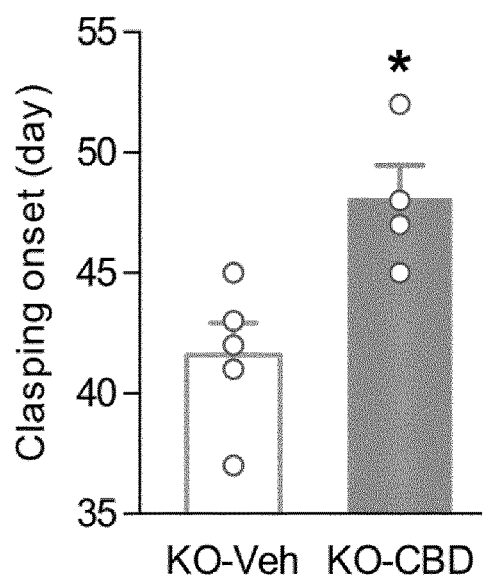
FIG. 2. Repeated CBD treatment delays the clasping onset in a mouse model of Leigh syndrome. The onset of clasping, a commonly reported phenotype that progresses with neurological decline and weight loss, was delayed in Ndufs4$^{-/-}$ mice daily treated with CBD (100 mg/kg, once daily) (KO-CBD) compared to vehicle-treated Ndufs4$^{-/-}$ mice (KO-Veh) $p<0.05$.

The appearance of clasping, a commonly reported phenotype that progresses with weight loss and neurological decline, was significantly delayed in Ndufs4$^{-/-}$ mice treated with CBD (KO-CBD) compared to vehicle-treated Ndufs4$^{-/-}$ mice (KO-Veh) $p<0.05$ (FIG. 2).

Figure 3:
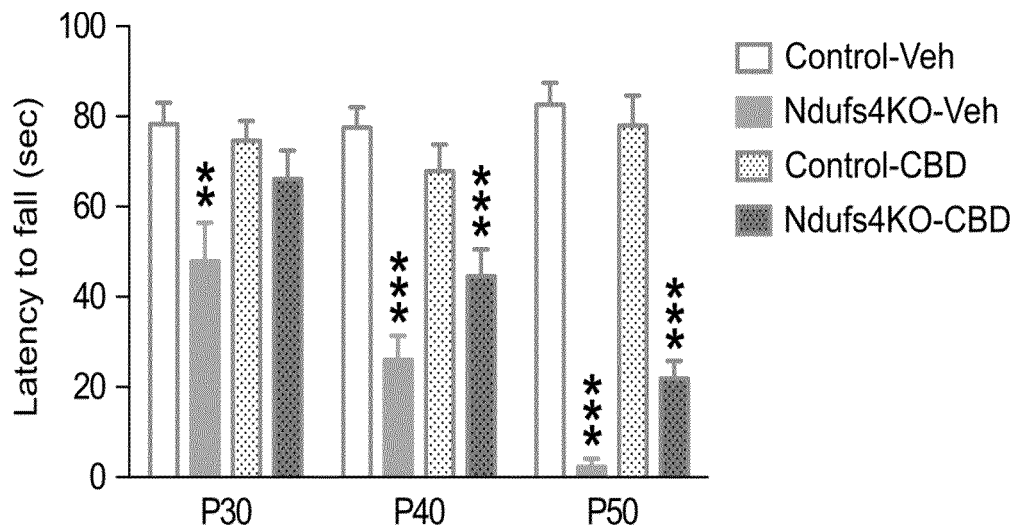
FIG. 3. Repeated CBD treatment attenuates the progressive decline in motor performance in a mouse model of Leigh syndrome. Accelerating rotarod performance of Ndufs4$^{-/-}$ mice and wild-type littermates treated with vehicle or CBD (100 mg/kg, once daily). Time to fall off is represented among the 3 tested days (postnatal day 30, 40, and 50). *$p<0.05$, ***$p<0.001$ vs control-veh.

The daily CBD treatment also delayed the progressive decline observed in Ndufs4KO mice performing a rotarod test, which measures motor coordination, balance, and endurance (FIG. 3).

Overall, these results state that CBD administration delays the appearance of impaired motor skills, the neurological decline, and ultimately the early death observed in Ndufs4$^{-/-}$ mice.

Given the early onset severe phenotype that results in death at a median age of ~40 days in Ndufs4$^{-/-}$ mice, it is difficult to study certain clinical signs that recapitulate some symptoms of the human pathology. Therefore, the inventors used the conditional knockout mice that lack Ndufs4 only in GABAergic cells in order to dissect specific clinical manifestations that are common in MD children such as epilepsy and autism. To do so, the inventors crossed the Gad2-Cre mouse line with the Cre-dependent Ndufs4$^{loxP/loxP}$ line to generate the cell type-specific conditional knockout mice (Gad2:Ndufs4cKO). These mice show normal body weight and no signs of motor impairments. However, recurrent seizures are observed from postnatal day 40 and more than 90% of mice die before postnatal day 70 generally due to a strong epileptic attack. Given the short half-life of CBD in rodents (~4.5 h) compared to humans (~24 h), CBD (100 mg/kg, intraperitoneal) was administered twice daily beginning at the period of seizure risk (postnatal day 35-40) in order maintain a minimum of plasma CBD concentration that might protect against spontaneous seizures.

Figure 4:
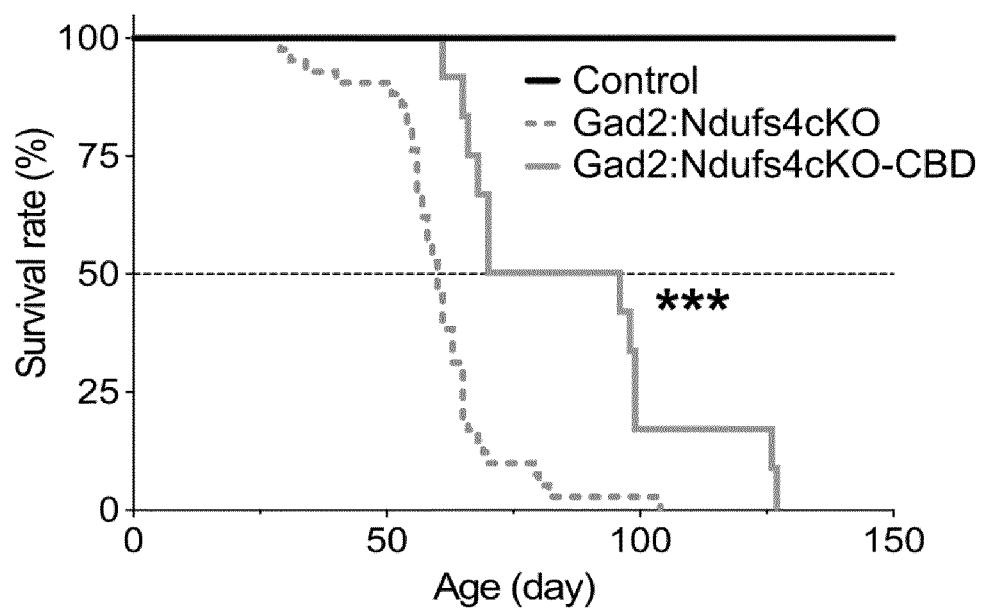
FIG. 4. Repeated CBD treatment improves survival in a cell type-specific mouse model of Leigh syndrome. Survival of the Gad2:Ndufs4cKO mice was extended by chronic CBD treatment (100 mg/kg, twice daily) (log-rank $p<0.0001$) (n=21 control mice; n=42 including both non-treated and vehicle treated-Gad2:Ndufs4cKO mice; n=12 CBD-treated Gad2:Ndufs4cKO mice).

Interestingly, repeated CBD treatment extended the life span of Gad2:Ndufs4cKO mice (FIG. 4). Compared to non-treated or vehicle treated-Gad2:Ndufs4cKO mice, CBD administration significantly increased the average survival time (60 versus 87 days survived in vehicle- and CBD-treated Gad2:Ndufs4cKO mice respectively; $p<0.0001$).

Figure 5:
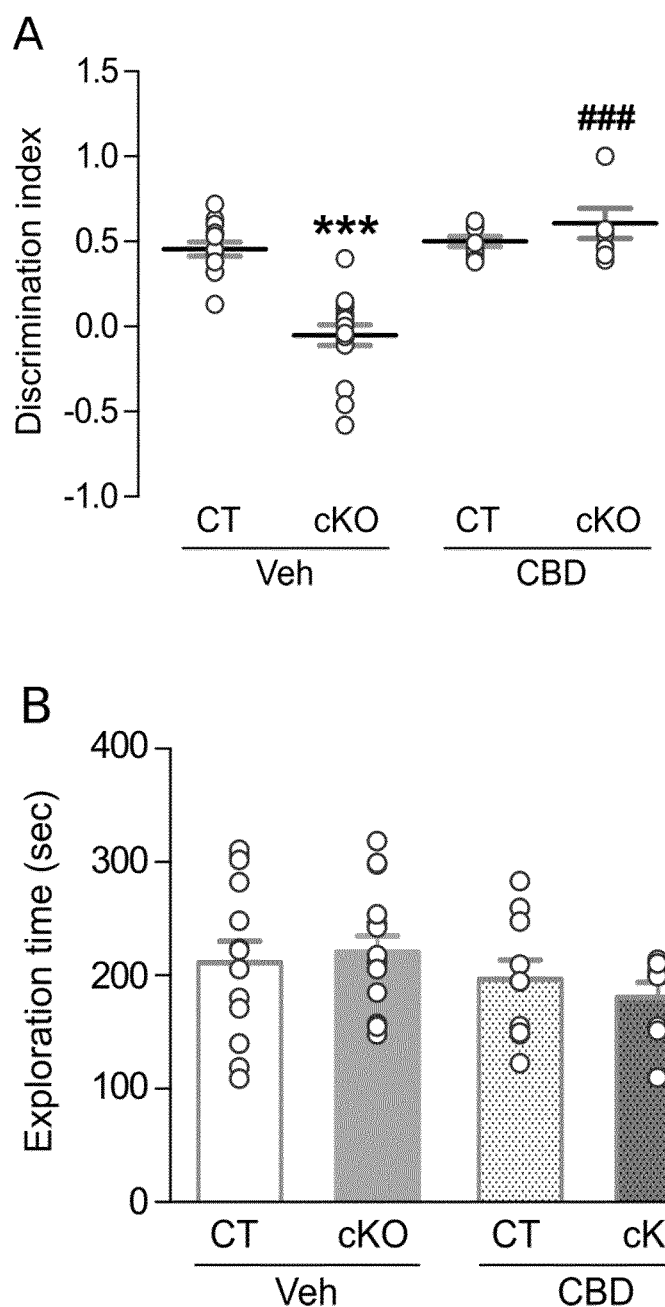
FIG. 5. Repeated CBD treatment improves social deficits in a cell type-specific mouse model of Leigh syndrome. (A) Discrimination index of the time exploring a stranger mouse versus an empty wire cage in the three-chamber social approach test and (B) total exploration time over 10 min of Gad2:Ndufs4cKO (cKO) and control mice (CT) treated with vehicle or CBD (100 mg/kg, twice daily) (n=8-16 mice/group). ***$p<0.001$ vs. control-veh, ###$p<0.001$ vs. Gad2:Ndufs4cKO-Veh.

The data shown above state that autism-spectrum range might be seen among other multi-system manifestations in primary MD more commonly than expected. The cell type-specific Gad2: Ndufs4cKO mice represent a good genetic model to study autistic-like behavior since these transgenic mice display profound social deficits compared to control mice (FIG. 5).

To test CBD's efficacy in treating decreased sociability, the inventors performed the three-chamber social approach test in Gad2:Ndufs4cKO mice and wild-type littermates repeatedly treated with CBD (100 mg/kg, twice/day). The non-treated and vehicle-treated Gad2:Ndufs4cKO mice were pooled, since their behavioral outcome was similar. The results show that CBD administered 1 h before testing reversed the autistic-like behavioral deficit observed in Gad2:Ndufs4cKO mice, as shown by an increased time spent exploring the stranger mouse compared to the object (FIG. 5). Importantly, CBD had no effect on control mice, suggesting that CBD significantly improves social interaction only in a genetic model of MD.

In summary, the results of the present disclosure allow new therapeutic approaches to mitochondrial diseases to be developed, through the use of CBD and pharmaceutical compositions comprising thereof.

The invention claimed is:

1. A method of treatment of Leigh syndrome (LS) comprising:
administering a compound of Formula I:

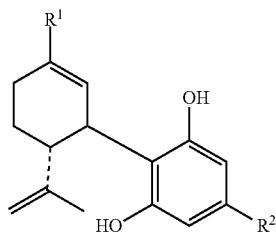

wherein:
$R^1$ is selected from $(C_1-C_5)$alkyl, —COOH and —CH$_2$OH; and
$R^2$ is selected from $(C_5-C_{12})$alkyl, —OR$^3$ and —(CH$_2$)$_n$—O—$(C_1-C_5)$alkyl; and wherein:
$R^3$ is selected from $(C_5-C_9)$alkyl or $(C_5-C_9)$alkyl substituted at the terminal carbon atom by a phenyl group; and
n is an integer from 1 to 7,
to a patient in need thereof.

2. The method of claim 1 wherein the compound is used in combination with at least one additional pharmaceutical active ingredient.

3. The method of claim 1 wherein the compound is used in the absence of tetrahydrocannabinol (THC).

4. A method of treatment of Leigh syndrome (LS) comprising:
administering a pharmaceutical composition comprising a therapeutically effective amount of a compound of Formula I:

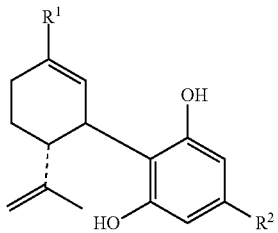

wherein:
$R^1$ is selected from $(C_1-C_5)$alkyl, —COOH and —CH$_2$OH; and
$R^2$ is selected from $(C_5-C_{12})$alkyl, —OR$^3$ and —(CH$_2$)$_n$—O—$(C_1-C_5)$alkyl; and wherein:
$R^3$ is selected from $(C_5-C_9)$alkyl or $(C_5-C_9)$alkyl substituted at the terminal carbon atom by a phenyl group; and
n is an integer from 1 to 7,
and a physiologically acceptable carrier or excipient, to a patient in need thereof.

5. The method of claim 4 wherein the composition further comprises at least one additional pharmaceutical active ingredient.

6. The method of claim 4 wherein the composition is devoid of tetrahydrocannabinol (THC).

7. The method of claim 5, wherein the additional pharmaceutical active ingredient is selected from the list consisting of: idebenone, and/or analogues or derivatives thereof, antioxidants and mixtures thereof.

8. The method of claim 4, wherein $R^1$ is $CH_3$ and $R^2$ is pentyl.

9. The method of claim 2, wherein the additional pharmaceutical active ingredient is selected from the list consisting of: idebenone, and/or analogues or derivatives thereof, antioxidants and mixtures thereof.

* * * * *